United States Patent [19]

Barbere

[11] Patent Number: 5,265,622
[45] Date of Patent: Nov. 30, 1993

[54] GUIDEWIRE HAVING RADIALLY EXPANDABLE MEMBER AND METHOD FOR GUIDING AND ADVANCING A CATHETER USING THE SAME

[75] Inventor: Michael D. Barbere, Dunstable, Mass.

[73] Assignee: C. R. Bard, Inc., Murray Hill, N.J.

[21] Appl. No.: 603,948

[22] Filed: Oct. 25, 1990

[51] Int. Cl.⁵ .............................................. A61M 25/00
[52] U.S. Cl. ......................................... 128/772; 604/96; 604/165; 604/164
[58] Field of Search ............... 604/282, 280, 264, 165, 604/164, 170, 96, 158; 128/772, 657, 656; 378/163, 162

[56] References Cited

U.S. PATENT DOCUMENTS

| | | | |
|---|---|---|---|
| 3,706,883 | 12/1972 | McIntyre | 378/163 |
| 3,996,938 | 12/1976 | Clark, III | 128/348 |
| 4,545,390 | 10/1985 | Leary | 604/96 X |
| 4,655,771 | 4/1987 | Wallsten | 604/282 X |
| 4,798,598 | 1/1989 | Bonello et al. | 604/280 |
| 4,808,163 | 2/1989 | Laub | 604/282 X |
| 4,813,934 | 3/1989 | Engelson et al. | 604/99 |
| 4,846,174 | 7/1989 | Willard et al. | 604/96 X |
| 4,848,344 | 7/1989 | Sos et al. | 128/344 |
| 4,922,924 | 5/1990 | Gambale et al. | 604/280 X |
| 4,932,959 | 6/1990 | Horzewski et al. | 606/194 |
| 4,994,032 | 2/1991 | Sugiyama et al. | 604/282 X |
| 5,002,560 | 3/1991 | Machold et al. | 606/198 |

FOREIGN PATENT DOCUMENTS 0371486 6/1990 European Pat. Off.
2020557 11/1979 United Kingdom.

*Primary Examiner*—Gene Mancene
*Assistant Examiner*—Jeffrey A. Smith
*Attorney, Agent, or Firm*—Wolf, Greenfield & Sacks

[57] ABSTRACT

A guidewire for use in guiding a catheter is provided with an expandable element at its distal region. The element may be expanded from a contracted configuration having a diameter corresponding to that of the guidewire and an expanded configuration larger than that diameter. A control element, such as a pull wire, extends through the guidewire from the proximal end of the guidewire and is associated with the expandable element to control expansion and contraction of the expandable element. The guidewire may be used in a number of modes. In one mode, the guidewire may be used to enhance the pushability of a catheter by locating the expandable element in the distal end of the lumen of the catheter and expanding the element at that location to lock the expandable element to the distal end of the catheter. Thereafter, the guidewire and catheter may be advanced in unison with the guidewire enhancing the pushability of the combination. In another mode of operation, the guidewire may be used with a single lumen balloon catheter in which the expandable element may be used both to enhance the pushability of the combination as well as to seal the distal end of the catheter to enable the balloon to be inflated and deflated through the catheter lumen.

11 Claims, 5 Drawing Sheets

GUIDEWIRE HAVING RADIALLY EXPANDABLE MEMBER AND METHOD FOR GUIDING AND ADVANCING A CATHETER USING THE SAME

FIELD OF THE INVENTION

This invention relates to catheters and guidewires for use with such catheters.

BACKGROUND OF THE INVENTION

A wide variety of medical procedures involve the use of a catheter. Typically, the catheter is of a special construction adapted particularly to perform the specific procedure. A typical catheter is in the form of an elongate flexible member, usually tubular, and is adapted to be passed through body passages and lumens to reach the intended site of treatment. The distal end of the catheter, which is disposed within the patient, may carry various devices or elements, among the more common of which is an inflatable balloon. The shape, material and characteristics of the balloon will vary depending on the particular procedure that the balloon is intended to perform. For example, such catheters are used in cardiovascular procedures, such as in angioplasty.

In angioplasty, the object is to widen the passageway through an obstructed or narrowed portion of an artery by inserting the balloon of a balloon dilatation catheter into the obstruction and then inflating the balloon under high pressure to forcibly dilate the obstruction. The angioplasty catheter includes an elongate flexible shaft having a dilatation balloon mounted to the distal end of the shaft. In one type of balloon angioplasty catheter, sometimes referred to as an "over the wire" or "moveable wire" catheter, the shaft has two lumens including a guidewire lumen that extends the full length of the shaft and is adapted to moveably receive a guidewire and an inflation lumen that extends from the proximal end of a shaft to the interior of the balloon for inflation and deflation of the balloon. In use, the catheter is manipulated and advanced through the patient's arteries to place the balloon at the treatment site. More specifically, the catheter is directed to the intended treatment site by cooperative use of the guidewire which is advanced through the patient's arteries to and through the site of the arterial obstruction (the stenosis) to be treated. After the guidewire is so positioned, the catheter then is pushed along the guidewire so that it advances toward the stenosis. The catheter is advanced until the balloon, which is in a deflated condition, is inside the stenosis. The balloon then is inflated under high pressure to forcefully dilate the stenosis and enlarge the flow area through the artery.

In general, it is more difficult to advance a catheter into the more distal arteries because those arteries are very narrow and present increased resistance to an advancing catheter. The arteries also may be very tortuous, which adds further to the difficulty of advancing the catheter. Generally, when it is desired to access a distal artery, it is necessary to use a smaller diameter catheter having a relatively low profile (reduced cross section), particularly in the area of the balloon which must be passed into the stenosis. Smaller diameter catheters, however, tend to have reduced column strength and may tend to buckle in accordion-like fashion when pushed against an artery or stenosis that presents significant resistance. Also, among the difficulties sometimes presented with angioplasty catheters is that the catheter may not track along the guidewire as desired. For example, if the stiffness of the catheter relative to the guidewire is too great then the advancement of the catheter may pull the guidewire out of position. Such difficulties in trackability may be exaggerated in tortuous or narrow arteries. It would be desirable, therefore, to provide a catheter and guidewire system that reduced the tendency for the catheter to collapse longitudinally when advanced through a tight stenosis, even when the catheter is of small diameter. It also would be desirable to provide such a catheter arrangement in an over the wire configuration that displays improved trackability characteristics.

As mentioned, angioplasty catheters that are intended to be used in the smaller distal arteries must have a low profile, particularly in the balloon area when the balloon is deflated. The low profile enhances the ability of the balloon region of the catheter to pass through small diameter blood vessels and into a tight stenosis. The extent to which the diameter of the catheter can be reduced, however, is limited by a number of factors, including the number of lumens in the catheter. As described above, a common construction for an angioplasty catheter includes an elongate flexible shaft having two lumens, including a guidewire lumen and an inflation lumen. The smallest diameter coronary angioplasty catheters having such a two lumen configuration is of the order of 0.040-0.055 inches diameter.

Another type of balloon angioplasty catheter is the "fixed-wire" type of catheter in which the catheter has a single lumen and is mounted directly and permanently on the guidewire, with the guidewire passing through the single lumen. Because such a catheter requires only a single lumen, it may be made in a smaller diameter than the two lumen catheters. Such fixed wire catheters, although providing a reduced profile, have presented some difficulties in steering and manipulation of the self contained guidewire. For example, among the problems presented has been that the balloon sometimes would become wrapped about the guidewire as the guidewire was rotated and manipulated. Additionally, typical fixed wire catheters do not permit a catheter exchange to be performed without losing guidewire position in the stenosis. It would be desirable, therefore, to provide an improved low profile single lumen catheter that avoids the foregoing difficulties.

SUMMARY OF THE INVENTION

In one aspect of the invention, a guidewire is provided with a radially expandable element adjacent its distal end. The degree of radial expansion is controllable from the proximal end of the guidewire, the element being contractible to the diameter of the guidewire. The guidewire thus can function as a conventional guidewire or can perform additional functions when the expandable element is expanded. For example, when a catheter is to be advanced through a small diameter artery or tight stenosis and in order to enhance the "pushability" of the catheter, that is, to reduce the tendency for the catheter to collapse longitudinally, the guidewire may be positioned so that the radially expandable element is disposed within and adjacent the distal end of the catheter. The radially expandable element then is expanded so that it engages firmly and grips the inner surface of the guidewire lumen. The catheter then can be advanced together with the guidewire by pushing both on the catheter and the guidewire.

By maintaining pressure on the guidewire, the force applied to the guidewire will be transferred to the distal end of the catheter so that the catheter will tend to be pulled through the stenosis. By pulling the catheter from its distal end, it is tensioned as it is drawn through the stenosis and thereby reduces the tendency for longitudinal collapse or buckling.

In one embodiment of this aspect of the invention, the radially expandable element may be in the form of a tubular helically braided wire mesh which is attached at its proximal end to a fixed portion of the guidewire and at its distal end to a longitudinally movable portion of the guidewire. When the mesh is extended longitudinally, it will assume a reduced diameter corresponding to the diameter of the guidewire. When the mesh cylinder is contracted longitudinally, it will increase in diameter so that it can engage the inner surface of the guidewire lumen. In another embodiment, the radially expandable element of the guidewire may be in the form of a resilient elastomeric sleeve which, when compressed axially, will expand radially.

In another aspect of the invention, adapted to provide a very low profile catheter, the radially expandable element of the guidewire and the catheter may be configured so that when the element is expanded, it will make a seal with the distal end of a single lumen catheter, at a location distally of the balloon. The catheter in this embodiment preferably is a single lumen catheter in which the lumen serves the dual purpose of receiving a movable guidewire and acting as an inflation/deflation lumen for the balloon. The catheter has a tubular shaft which defines a single through lumen, open at the distal tip of the catheter, and a balloon attached to or formed on its distal end. In use, the guidewire first is manipulated to position its distal end through the stenosis to be treated, the radially expandable element of the guidewire being in a contracted configuration during this part of the procedure. Once the guidewire is placed, the catheter is advanced over the guidewire to place the balloon in the stenosis. The single lumen construction of the catheter enhances its flexibility and, therefore, results in a more trackable catheter as the catheter advances over the guidewire. It may be possible, during advancement of the balloon through the stenosis, to expand the radially expandable element of the guidewire into engagement with the lumen to enhance the pushability of the system as described above. After the balloon has been placed within the stenosis, the guidewire is positioned so that its radially expandable element is within the guidewire lumen of the catheter, at a location that will block liquid flow out of the catheter distally of the balloon. The radially expandable element then is expanded with inflation liquid to seal the distal end of the catheter lumen. The inflation liquid then is pressurized to inflate the balloon while the radially expandable element is maintained in its expanded, sealing configuration. The pressure of the inflation liquid is increased sufficiently to effect the dilatation.

It is among the general objects of the invention to provide improved catheter and guidewire systems in which the guidewire has an expandable segment to engage the guidewire lumen of the catheter.

Another object of the invention is to provide catheter and guidewire systems which avoid the tendency of the catheter to collapse longitudinally when the catheter is pushed through a narrow or stenosed blood vessel or stenosis.

A further object of the invention is to provide an improved catheter and guidewire system in which the guidewire can be firmly engaged with the distal end of the catheter so that by pushing on the guidewire, the distal end of the catheter is pulled, thereby avoiding longitudinal collapse of the catheter.

Another object of the invention is to provide a single lumen, low profile, over the-wire balloon catheter having a multifunction single lumen adapted to receive a guidewire as well as to serve as an inflation and deflation lumen for the balloon and further in which the guidewire may be controlled to effect a seal against the inner surface of the lumen distally of the balloon.

A further object of the invention is to provide a guidewire with an expandable element that seals the lumen of a catheter.

An additional object of the invention is to provide a single lumen, low profile, over the wire balloon catheter having a multifunction single lumen adapted to receive a guidewire which displays improved trackability of the catheter over the guidewire.

Another object of the invention is to provide a guidewire having an expansible element that is controllable from the proximal end of the guidewire.

DESCRIPTION OF THE DRAWINGS

The foregoing and other objects and advantages of the invention will be appreciated more fully from the further description thereof, with reference to the accompanying drawings wherein.

DESCRIPTION OF THE PREFERRED EMBODIMENT

Figure 1:
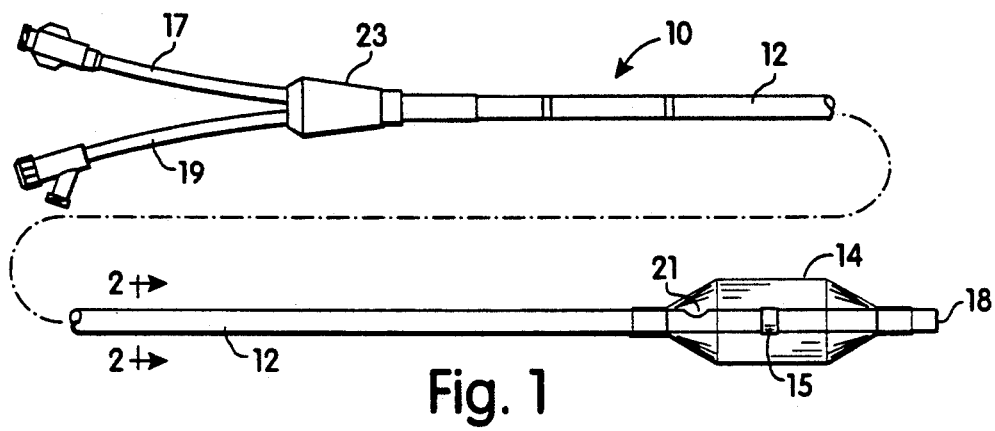
FIG. 1 is a somewhat diagrammatic, fragmented illustration of a two lumen over-the-wire dilatation catheter with which the invention may be used.
Figure 2:
FIG. 2 is a sectional illustration of the catheter shaft of FIG. 1 as seen along the line 2—2 of FIG. 1.

FIGS. 1 and 2 illustrate one type of a two lumen dilatation catheter, indicated generally by the reference character 10, with which the present invention may be used. It should be understood, however, that the invention also may be used with other types of over-the wire dilatation catheters, such as those in which the two lumens are concentric and are defined by generally coaxial tubes. The catheter may include an elongate flexible polymeric shaft 12 having a balloon 14 attached to the distal end of the shaft. The shaft 12 has two lumens including a guidewire lumen 16 that extends from the proximal end of the shaft to the distal tip and terminates in an outlet orifice 18. The other lumen serves as an inflation/deflation lumen and extends from the proximal end of the catheter to the balloon, where the distal end of the lumen 20 communicates with the interior of the balloon 14 via a port indicated diagrammatically in phantom at 21 in FIG. 1. The proximal end of the catheter is provided with a bifurcation 23 to provide independent communication with each of the lumens 16, 20, such as through tubular legs 17, 19, as is well known in the art. Tubular leg 17 communicates with the inflation lumen 20 and has a fitting at its proximal end for connection to an inflation and deflation device, such as a syringe. Tubular leg 19 communicates with the guidewire lumen 16 and has, at its proximal end, a Y fitting having one leg adapted to receive a guidewire in sealed relation and another leg defining a fluid connection so that it may be connected to pressure monitoring equipment or fluid infusion equipment.

By way of example, a typical dilatation catheter adapted for use in the coronary arteries may have a shaft with an outer diameter of the order of 0.040-0.055 inches. The inner dimensions of the guidewire lumen 16 typically may be of the order of 0.020" in effective diameter, that is, adapted to receive a small diameter guidewire of a diameter less than about 0.020". When the catheter is intended for use in the coronary arteries, it will have a length of the order of 150 cm. By way of further example, the catheter may be of a construction illustrated generally in U.S. Pat. No. 4,545,390 (Leary) to which reference is made and which is incorporated herein by reference.

Figure 8:
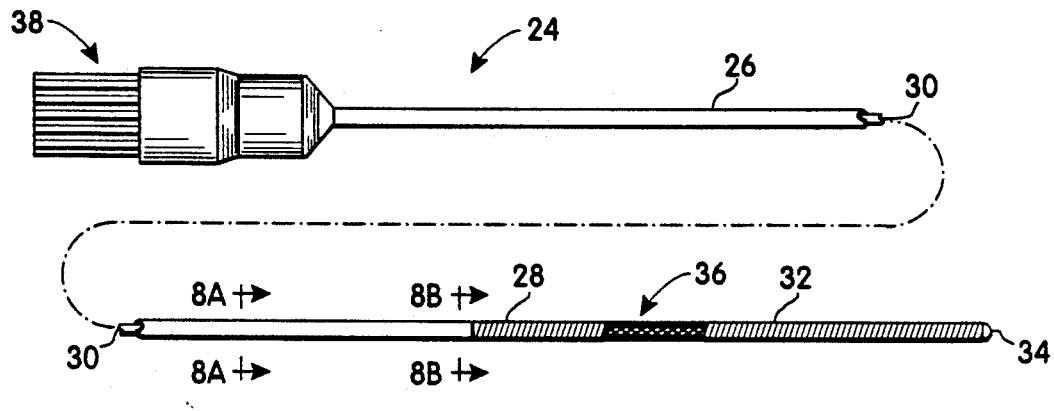
FIG. 8 is an illustration of another embodiment of the invention in which the radially expandable element of the guidewire is in the form of a cylindrical wire mesh.
Figure 9:
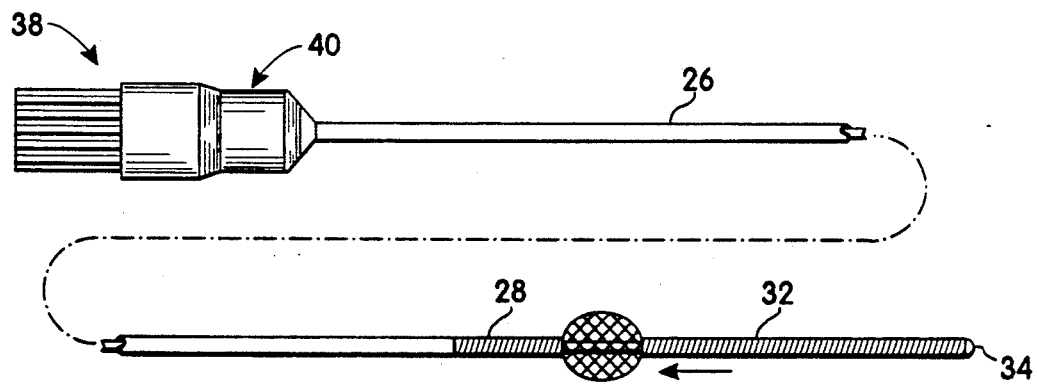
FIG. 9 is an illustration of the embodiment as shown in FIG. 8 with the expandable mesh in expanded configuration.

In accordance with the invention, FIGS. 8 and 9 illustrate one embodiment of a guidewire having a radially expandable element. The guidewire may be of the order of 175-180 cm long and may have an outer diameter of the order of 0.014"-0.018" so that it may pass easily through the guidewire lumen 16 of the catheter. In the preferred embodiment, the guidewire is formed from a length of stainless steel tubing 26, commonly referred to as hypodermic tubing, having an outer diameter of the order of 0.014 to 0.018 inches and having a wall thickness of the order of 0.002 to 0.003 inches. The hypodermic tubing may be about 145 cm long. A proximal helical coil 28 is attached to the distal end of the hypodermic tubing 26 and may extend over a length of about 20 cm. The guidewire 24 includes a core wire 30 that extends through the lumen of the hypodermic tubing and the proximal helical coil 28, the core wire 30 extending approximately 35 cm beyond the distal end of the hypodermic tubing 26. A distal helical coil 32, approximately 10 cm long is attached at its distal end, as by a tip weld 34, to the distal tip of the core wire 30. The coils may be formed from stainless steel or other suitable, more radiopaque wire, for example, of about 0.002" to 0.003" diameter.

The proximal and distal coils 28, 32 are dimensioned with respect to the core wire so that the distal end of the proximal coil 28 and the proximal end of the distal coil 32 are spaced. In this embodiment the space between the proximal and distal coils is occupied by a helical wire mesh cylindrical element indicated generally at 36. The helical mesh cylindrical element 36 is formed from a plurality of helically braided strands formed, for example, from stainless steel wire 0.002 to 0.003 inches diameter. The braided strands are arranged so that the length of the element 36 can be varied. As illustrated in FIG. 8 when the mesh element 36 is tensioned, it will contract to a diameter corresponding to the 0.014" to 0.018" outer diameter of the guidewire. When contracted, however, as illustrated in FIG. 9, the wire mesh element 36 expands radially.

The core wire 30 is movable longitudinally within the guidewire to shift the position of the distal helical coil 32 distally or proximally with respect to the proximal coil 28. By so moving the core wire and distal coil, the wire mesh element 36 can be expanded or contracted, as controlled from the proximal end of the guidewire. The element 36 is constructed so that it can expand radially to a diameter slightly greater than the dimension of the guidewire lumen, for example, to about 0.022" diameter. When the guidewire is disposed within the catheter, the wire mesh element 36 may be expanded into firm engagement with the inner surface of the lumen to lock the guidewire to the inner lumen or, alternately, can be contracted to enable the guidewire to function in its normal manner, to serve as a positioning and guiding element for the catheter.

Figure 6:
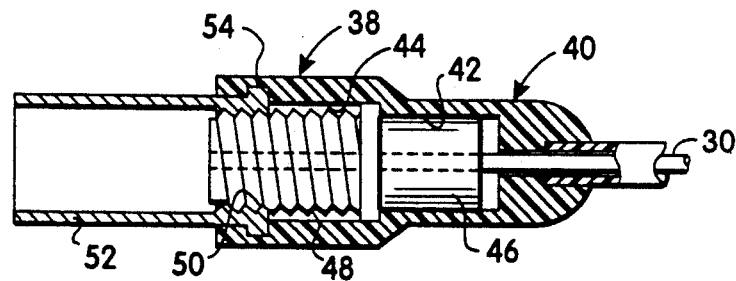
FIG. 6 is an enlarged illustration of the control device at the proximal end of the guidewire for controlling expansion of the expandable element and in a configuration in which the expandable element is contracted.
Figure 7:
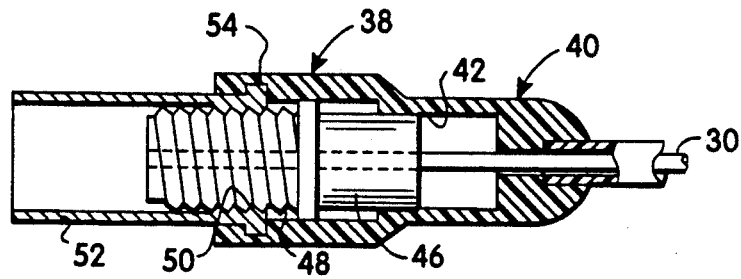
FIG. 7 is an enlarged sectional illustration similar to FIG. 6 showing the configuration of the device when the radially expandable element is in an expanded configuration.

In order to facilitate control of the relative position of the helical coils 28, 32, the proximal end of the guidewire may be provided with a core wire pull mechanism indicated generally at 38. As shown in FIGS. 6 and 7, the core wire pull mechanism 38 includes a fitting 40 securely attached to the proximal end of the tubular shaft 26. The fitting 40 may include an inner bore 42 and a larger diameter outer bore 44. A plug 46 is slidably and rotatably received in the inner bore 42. A threaded stem 48 is attached to the proximal end of the plug 46. The threaded stem 48 is received in a threaded hole 50 in the distal end of a rotatable control member 52. The control member 52 may have a circumferential collar 54 received in a circumferential groove formed at the inner surface of the outer bore 44, as shown. The collar 54 retains, rotatably, the control member 52. The proximal end of the pull wire 30 is attached to the plug 46 and/or threaded stem 48. From the foregoing, it will be appreciated that as the rotatable control element 52 is rotated, the plug and stem will be shifted axially thereby applying tension or some compression, or at least relaxation of the tension, on the core wire 30. The parts of the pull mechanism 38 may be formed from a suitable metal or polymeric material as desired.

Figure 11:
FIG. 11 is an enlarged illustration of the reduced diameter distal end of the pull wire of the guidewire.

The distal end of the core wire preferably is tapered, either in a continuous or a step taper, so that the distal end of the core wire presents a more flexible, atraumatic tip. FIG. 11 illustrates a step tapered configuration which may be used in the invention. The configuration includes a distal tapered segment 56 about 5 cm long having a diameter of about 0.006" at its proximal end and tapering to a distal tip diameter of the order of 0.002". Proximally of the tapered tip segment 56 is a uniform diameter barrel segment 58, about 18 cm long and having a diameter of 0.006". Proximally of the barrel segment 58 is a proximal tapered segment 60, about 6 cm long and having a diameter at its proximal end of about 0.008 to about 0.009 inches diameter. Proximally of segment 60, the core wire 30 is of uniform diameter to its point of connection at the control device.

Figure 8B:
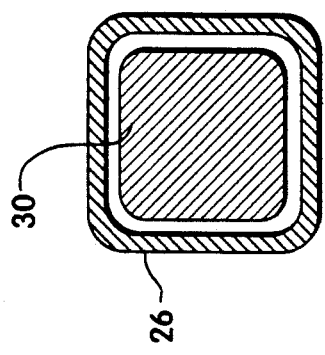
FIG. 8B is an illustration of the guidewire of FIG. 8 as seen along the plane 8B—8B of FIG. 8.
Figure 8A:
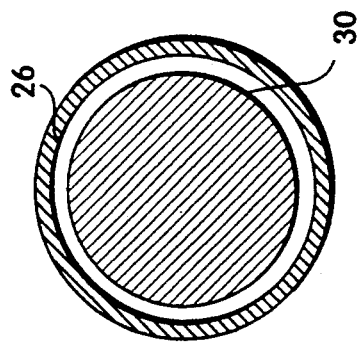
FIG. 8A is a cross-sectional illustration of the guidewire as seen along the line 8A—8A of FIG. 8.

In order to facilitate the transmission of torque from the proximal to the distal end of the guidewire, the core wire 30 and the tubing 26 from which the guidewire is made may be swaged or otherwise deformed to a non circular cross-sectional configuration at the distal end of the tubing 26. Thus, as shown in FIG. 8A, it may be seen that the tubing 26 and core wire 30 both are circular along substantially the full length of the tubing 26 except for a short distal segment, shown in cross-section in FIG. 8B in which both the core wire 30 and the tubing 26 have been swaged to a non-circular shape. Thus, FIG. 8B illustrates, diagrammatically, such a non-circular shape in the form of a square cross section. It should be understood, however, that other non-circular cross sectional configurations such as oval, star, fluted and the like may be employed. The non circular cross sectional configuration at the distal end of the tubing 26 should be such as to permit axial movement of the core wire 30 with respect to the tubing 26, in order to actuate the expanding member 36. The non-circular cross-section should be such as to resist rotation of the core wire with respect to the tubing 26. Thus, the rotation of the tube will apply torque to the core wire and at the distal end of the tube 26. The core wire thus will rotate in unison with the tubing 26 so that rotation may be transmitted to the distal tip of the guidewire through that portion of the core wire that extends through the helical coils.

Figure 3:
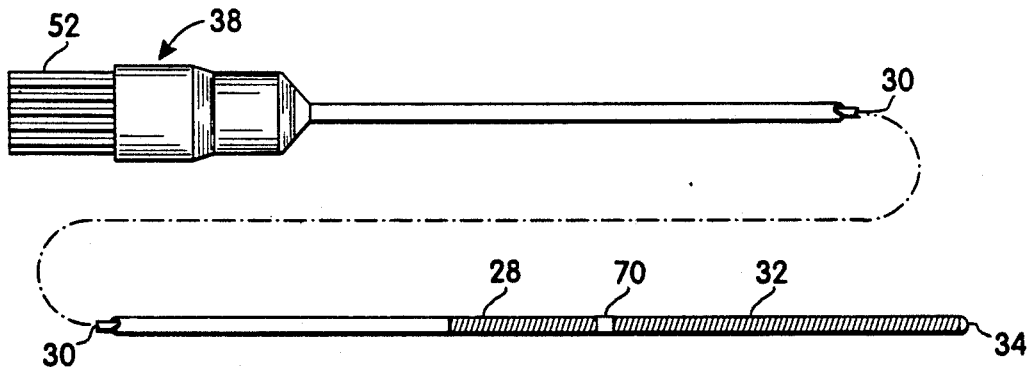
FIG. 3 is a fragmented somewhat diagrammatic illustration of one embodiment of a guidewire in accordance with the invention in which the radially expandable element is in a contracted configuration.
Figure 4:
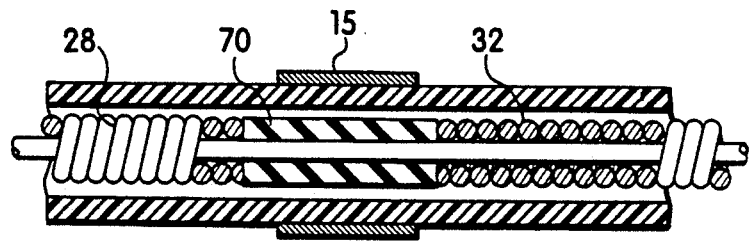
FIG. 4 is an enlarged illustration of one embodiment of the radially expandable element of the guidewire in its contracted configuration and disposed within the guidewire lumen of the catheter.
Figure 5:
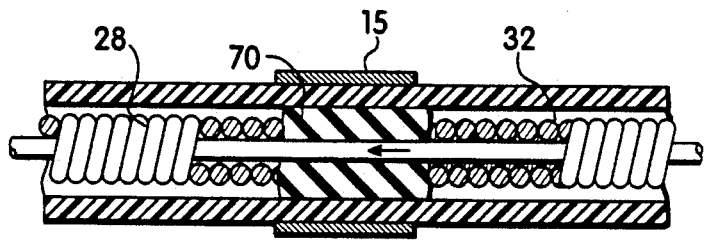
FIG. 5 is an illustration of the guidewire of FIG. 3 with the radially expandable element in an expanded configuration.

FIG. 3 illustrates another embodiment of the invention in which the guidewire has a radially expandable element in the form of a compressible elastomeric sleeve. In this embodiment of the invention, the construction of the guidewire is similar to that described above in connection with the embodiment of FIGS. 8 and 9 except that the radially expandable member is int he form of an elastomeric sleeve 70. The sleeve 70 has a central aperture by which it is mounted on the core wire 30. The sleeve 70 is disposed between the proximal and distal helical coils 28, 32. The core wire 30 extends through the guidewire and is attached to the distal tip of the distal helical coil, at the tip weld, as described above in connection with the embodiments of FIGS. 8 and 9. As in the embodiments of FIGS. 8 and 9, the proximal end of the proximal helical coil is soldered to the distal end of the hypodermic tubing and the distal end of the core wire is soldered to a tip bead 34. The expandable member preferably is a silicone, elastomeric sleeve having a relaxed diameter corresponding to that of the guidewire and an expanded diameter of the order of 0.022". As in the embodiment described in connection with FIGS. 8 and 9, the expandable member is caused to expand radially by pulling on the core wire which draws the coils together to compress the expandable member.

In the embodiment illustrated in FIGS. 1-5, an additional advantage may be obtained by forming the helical coils 28, 32 from radiopaque material. Thus, the catheter 10 may be provided with a radiopaque marker band 15. The marker band 15 preferably is of a length corresponding generally to the elongated lengthwise dimension of the expandable element 70. With that configuration, it is possible to locate precisely the guidewire with respect to the catheter using X ray fluoroscopy. Thus, as suggested in FIGS. 4 and 5, it will be appreciated that when the expandable element 70 is disposed in the region of the balloon and, more particularly, at the location of the marker band 15, the X ray image presented on the fluoroscope will be a continuous dark line. That results from the continuous radiopaque image presented by the proximal coil 28, marker band 15 and distal coil 32. Should the guidewire be disposed in any other position with respect to the catheter, the guidewire, in the region of the expandable element 70 will present a space in the radiopaque line of the guidewire, indicating the location of the space between the coils 28, 32. Thus, by manipulating the guidewire under fluoroscopy, the guidewire may be accurately and precisely placed by advancing the guidewire to present a continuous fluoroscopic image. It should be noted, however, that placement of the marker band 15 at the center of the balloon is but one possible location. It may be preferable in other instances to locate the marker band 15 at some other place on the catheter and, possibly, to locate the expandable element 70 on the guidewire more proximally or more distally along the guidewire.

Figure 10:
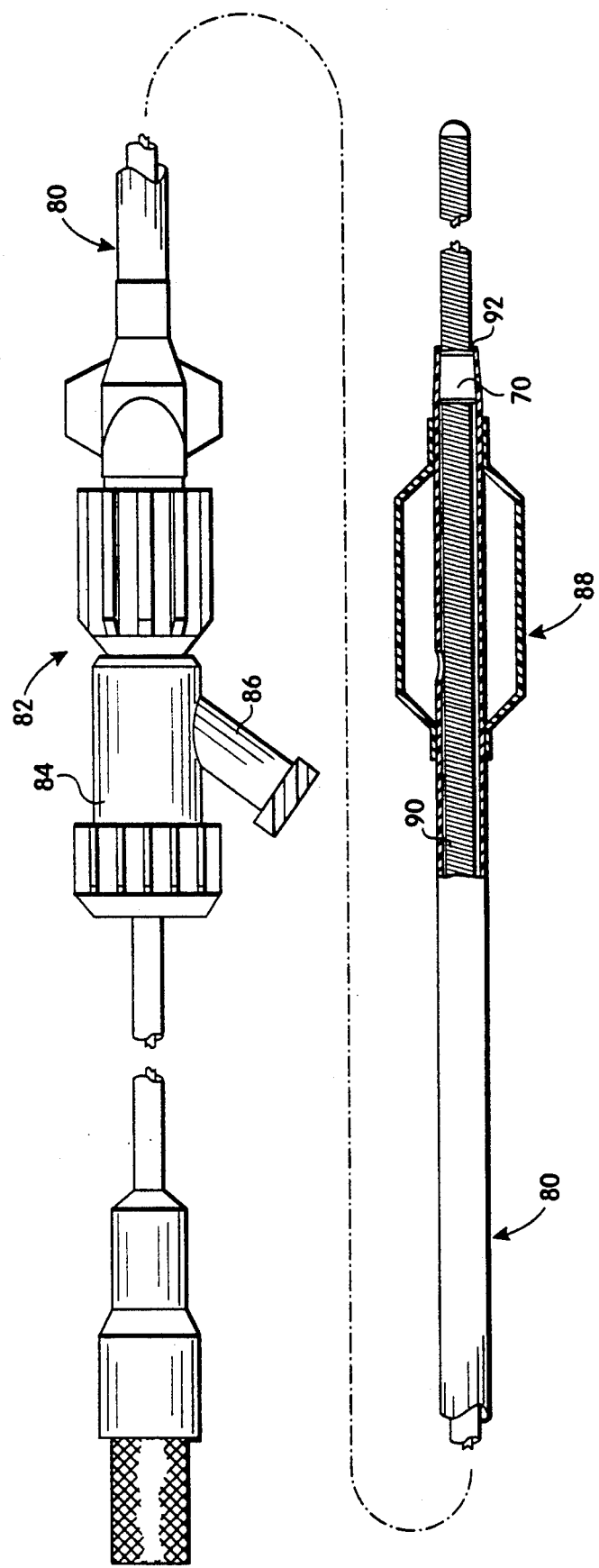
FIG. 10 is an illustration of one embodiment of a single lumen catheter intended to be used with a guidewire of the type illustrated in FIGS. 4 and 5 having a radially expandable occluder element, with the catheter incorporating a catheter shaft and a separate inflatable balloon mounted to the shaft and illustrating the expandable member of the guidewire in its expanded configuration, occluding the distal outlet of the lumen of the catheter shaft.

FIG. 10 illustrates another aspect of the invention in which a low profile single lumen balloon dilatation catheter is adapted to have conventional movable guidewire capability but in which the guidewire also carries a radially expandable element adapted to seal off the distal end of the catheter lumen, beyond the balloon, so that the balloon may be inflated and pressurized to perform a dilatation. The catheter includes an elongate flexible tubular shaft 80 formed from an appropriate polymeric material such as high density polyethylene. A Y-fitting 82 is attached to the proximal end of the catheter shaft. One branch 84 of the Y-fitting 82 is adapted to receive a guidewire in a sealed relation, as by a compressible gasket, such as a Tuohy Borst type of device, while the other branch 86 of the Y-fitting is intended to be connected to an inflation device for inflation and deflation of the balloon. The distal end of the catheter is provided with a balloon element 88 attached to the shaft as shown. The balloon may be formed from a variety of polymeric materials such as polyethylene terephthalate, polyethylene and the like, as is well known in the art. The catheter has a single lumen 90 which extends fully through the shaft 80 and the balloon 88 and opens at a distal orifice 92 at the distal tip of the catheter. The catheter is used in conjunction with a guidewire of the type described above and illustrated in FIGS. 3, 4 and 5.

In use, the guidewire, with its expandable element 70 in a contracted configuration, may be manipulated through the patient's arteries to place the distal tip of the guidewire through the stenosis to be treated. The single lumen catheter then may be advanced over the guidewire to place the balloon portion, in a deflated condition, through the stenosis. In order to assist advancement of the catheter through the stenosis, the radially expandable element 70 of the guidewire may be expanded into engagement with the distal end of the catheter to enhance the pushability of the catheter and improve its column strength as described previously. Once the balloon is disposed in the stenosis, the catheter is filled with inflation liquid, typically a radiopaque liquid, and when the catheter shaft and balloon are filled, the radially expandable element 70 is expanded into sealed relation with the catheter lumen distally of the balloon. With the distal outlet 92 so sealed, the pressure of the inflation liquid then may be increased sufficiently to effect the dilatation of the stenosis.

By way of example, the catheter shaft may be of the order of 135 cm long and may have an internal diameter of the order of 0.018 to 0.020 inches and an outer diameter of about 0.026 to 0.028 inches. The catheter thus defines a very low profile and is adapted to be advanced into and through narrow tortuous arteries such as the coronary arteries. The inner lumen of the catheter, particularly at the distal end, is dimensioned such that when the expandable element 70 on the guidewire is expanded, it will engage the inner lumen in a snug sealed manner.

From the foregoing, it will be appreciated that the invention provides improved catheter and guidewire systems adapted to enhance the pushability of the catheter-guidewire combination, and particularly with small diameter catheters that otherwise would tend to have relatively little column strength. Additionally, the systems enable a very small diameter single lumen catheter to be used in which a guidewire may serve in its catheter guiding function as well as in a manner to cooperate with the catheter during inflation and deflation of the balloon.

It should be understood, however, that the foregoing description of the invention is intended merely to be illustrative thereof and that other embodiments, modifications and equivalents of the invention may be apparent to those skilled in the art without departing from its spirit.

Having thus described the invention what I desire to claim and secure by Letters Patent is:

1. In a guidewire for use with a catheter, the guidewire having a shaft with a distal and a proximal end, the improvement comprising:
   an expandable, non-detachable, resilient element mounted on the distal end of the guidewire, the expandable element being radially expandable from a contracted configuration in which the element is not greater in diameter than the diameter of the guidewire shaft and an expanded configuration in which the diameter of the element is greater than that of the guidewire shaft, the expandable element being self-contractable under the influence of its inherent resilience;
   a control element extending from the proximal to the distal end of the guidewire for controlling expansion and contraction of the expandable element;
   the expandable element being elastomeric and compressible.

2. A guidewire for use with a catheter comprising:
   an elongate flexible tubular shaft having a proximal portion and a distal portion;
   a control element extending through the shaft form the proximal portion toward the distal portion;
   a resilient, radially expandable, non-detachable member mounted on the shaft, the member being self-contracting to a contracted configuration under the influence of its inherent resilience, the member being controllable so as to be expanded radially from said contracted configuration to a diameter greater than the diameter of the shaft, the expandable member being controllable by the control element, the radially expandable member being located on the guidewire so that when the guidewire is advanced fully into the catheter the radially expandable member will be disposed within the catheter;
   the control element comprising a pull wire with a proximal end and a distal end extending through the tubular shaft, the distal end of the pull wire being operatively associated with the expandable member;
   the expandable member comprising an elastomeric sleeve mounted along the shaft and where operation of the control wire is operative to compress or relax the sleeve.

3. A catheter and guidewire therefore, in combination, comprising:
   the catheter having an elongate flexible shaft having at least one lumen extending lengthwise through the shaft;
   the guidewire having a distal end and a proximal end and having an expandable, non-detachable element mounted on its distal end, the element being expandable to a dimension such that when it is disposed in the lumen of the catheter, it can be expanded to interfere with and securely engage the surface of the lumen;
   a control element at the proximal end of the guidewire for controlling the expansion and contraction of the element;
   the catheter having a single lumen and a balloon mounted on the distal end of the catheter shaft, the interior of the balloon being in fluid communication with the lumen, the lumen being open at the distal end of the shaft distally of the balloon;
   the lengths of the catheter and guidewire and the location of the expandable element on the guidewire being such that the guidewire may be inserted into the catheter with the expandable element disposed in the lumen of the catheter distally of the balloon.

4. A guidewire for use with a catheter comprising:
   an elongate flexible tubular shaft having a proximal portion and a distal portion;
   a control element extending through the shaft form the proximal portion toward the distal portion;
   a resilient, radially expandable, non-detachable member mounted on the shaft, the member being self-contracting to a contracted configuration under the influence of its inherent resilience, the member being controllable so as to be expanded radially from said contracted configuration to a diameter greater than the diameter of the shaft, the expandable member being controllable by the control element, the radially expandable member being located on the guidewire so that when the guidewire is advanced fully into the catheter the radially expandable member will be disposed within the catheter;
   the control element comprising a pull wire with a proximal end and a distal end extending through the tubular shaft, the distal end of the pull wire being operatively associated with the expandable member;
   a portion of each of the tubular shaft and pull wire being non-circular in cross-section and being constructed to permit relative axial movement between the pull wire and the tubular shaft thereby to preclude relative rotation between the pull wire and the proximal shaft while permitting relative axially movement therebetween.

5. A guidewire for use with a catheter comprising:

an elongate flexible tubular shaft having a proximal portion and a distal portion;

a control element extending through the shaft form the proximal portion towards the distal portion;

a radially expandable, non-detachable member mounted on the shaft and being controllable so as to be expanded radially from a contracted configuration to a diameter greater than the diameter of the shaft, the expandable member being controllable by the control element;

the shaft further comprising an elongate flexible length of substantially torsionally rigid tubing adapted to transmit rotation from the proximal portion to the distal portion;

a proximal helical coil having a proximal end and a distal end being attached at the proximal end thereof to the distal end of the tubing, the pull wire extending through the tubing and through the coil;

a distal coil carried by the distal end of the pull wire, the distal end of the pull wire being attached to the distal end of the distal coil;

the radially expandable member being mounted about the pull wire being the proximal and distal coils.

6. A guidewire as defined in claim 5 wherein the distal portion of the pull wire is of reduced diameter configuration compared to the proximal portion so as to be more flexible.

7. A guidewire as defined in claim 6 wherein the distal end of the pull wire is step tapered.

8. A method for advancing a catheter comprising:

providing a catheter with a proximal portion and a distal portion having a guidewire lumen;

providing a guidewire with a proximal end and a distal end having an expandable element carried at the distal end thereof;

inserting the guidewire into the catheter lumen so that the expandable element is disposed within the distal portion of the catheter lumen;

expanding the expandable element to cause the expandable element to securely engage the catheter by engagement with the surface of the catheter lumen; and while the catheter and guidewire are so engaged, advancing the catheter by advancing the guidewire whereby the connection between the guidewire and catheter will cause advancement of the catheter.

9. A method for guiding and inflating a balloon catheter through a body lumen comprising:

providing a catheter having an elongate flexible shaft open at its distal end and a balloon mounted adjacent the distal end of the catheter shaft and in communication with the lumen;

providing a guidewire having an elongate flexible tubular shaft having a proximal portion and a distal portion, a control element extending through the shaft from the proximal portion toward the distal portion, and a radially expandable non-removable member mounted on and fixed to the shaft and being controllable so as to be expanded radially from a contracted configuration to a diameter greater than the diameter of the shaft, the expandable member being controllable by the control element;

advancing the guidewire through the body lumen while manipulating the guidewire to locate the distal end of the guidewire in a predetermined location in the body lumen;

locating the catheter on the guidewire such that the expandable member of the guidewire is disposed distally of the proximal end of the balloon;

expanding the expandable member on the guidewire to occlude the lumen of the shaft to prevent flow of inflation liquid out of the distal end of the lumen;

thereafter applying liquid under pressure to the interior of the lumen and the balloon while maintaining the distal end of the lumen sealed.

10. A method as defined in claim 9 further comprising:

thereafter contracting the expandable element.

11. A method for guiding and advancing a catheter through a body lumen comprising:

providing a catheter having an elongate flexible shaft open at a distal end;

providing a guidewire having an elongate flexible tubular shaft having a proximal portion and a distal portion, a control element extending through the shaft from the proximal portion toward the distal portion, and a radially expandable, non-removable member mounted on and fixed to the shaft and being controllable so as to be expanded radially from a contracted configuration to a diameter greater than the diameter of the shaft, the expandable member being controllable by the control element;

advancing the guidewire through the body lumen while manipulating the guidewire to locate the distal portion of the guidewire in a predetermined location in the body lumen;

locating the catheter on the guidewire such that the expandable member of the guidewire is disposed within a distal region of the catheter;

expanding the expandable member on the guidewire to secure the guidewire to the distal region of the catheter and while so secured, advancing the guidewire and catheter together through the body lumen.

* * * * *